United States Patent
Shinya et al.

[11] Patent Number: 5,516,949
[45] Date of Patent: May 14, 1996

[54] DIFLUOROETHYLENE COMPOUNDS AND LIQUID CRYSTAL COMPOSITIONS CONTAINING THEM

[75] Inventors: Seiji Shinya; Osamu Yokokouji; Takashi Miyajima; Hidemasa Koh, all of Yokohama; Katsutoshi Machida, Samukawa, all of Japan

[73] Assignees: Asahi Glass Company Ltd., Tokyo; Seimi Chemical Co., Ltd., Chigasaki, both of Japan

[21] Appl. No.: 29,602

[22] Filed: Mar. 11, 1993

[30] Foreign Application Priority Data

Mar. 13, 1992 [JP] Japan .................................. 4-089982

[51] Int. Cl.$^6$ .................................................. C07C 19/08
[52] U.S. Cl. .................................... 570/128; 252/299.630
[58] Field of Search ............................................. 570/128

[56] References Cited

FOREIGN PATENT DOCUMENTS 3-294386  12/1991  Japan .

OTHER PUBLICATIONS

CA120: 285950 1992 (EP 9221734 Bartmann).
CA112: 46254 1989 (EP 325796 Kitano).
Database WPIL, Derwent Publications Ltd., AN 91–104778, JP–A–3 041 037, Feb. 21, 1991.

*Primary Examiner*—Gary Geist
*Assistant Examiner*—Catherine Kilby Scalzo
*Attorney, Agent, or Firm*—Oblon, Spivak, McClelland, Maier & Neustadt

[57] ABSTRACT

A difluoroethylene compound of the following formula (1):

$$R^1-(A^1)_m-Y^1-A^2-CF=CF-A^3-Y^2-(A^4)_n-R^2 \qquad (1)$$

wherein $A^3$ is a trans-1,4-cyclohexylene group, and each of $A^1$, $A^2$ and $A^4$, which are independent from one another, is a trans-1,4-cyclohexylene group or a 1,4-phenylene group, wherein each of such cyclic groups is unsubstituted or substituted by one or more halogen atoms or cyano groups, one or more =CH— groups constituting rings of such cyclic groups may be substituted by nitrogen atoms, and one or more —CH$_2$— groups constituting rings of such cyclic groups may be substituted by oxygen atoms or sulfur atoms.

1 Claim, No Drawings

DIFLUOROETHYLENE COMPOUNDS AND LIQUID CRYSTAL COMPOSITIONS CONTAINING THEM

The present invention relates to difluoroethylene compounds and liquid crystal compositions containing them.

Liquid crystal display devices have been used for watches and electronic calculators and in recent years for various applications including measuring devices, automobile meters, copying machines, cameras, display devices for office appliances and display devices for consumer products. Accordingly, various functions including a wide temperature range for operation, a low voltage for driving, a high response speed, a high contrast ratio, a wide visual angle and chemical stability, are required for such liquid display devices.

However, at present, there is no single material which by itself satisfies all of such requirements, and it is common to satisfy such requirements by a liquid crystal composition prepared by mixing a plurality of liquid crystal materials and non-liquid crystal materials. Accordingly, it is desired to develop a liquid crystal material or a non-liquid crystal material which is excellent in one or more functions, if not in all the required functions.

In the field of the display device using liquid crystal, it is desired to improve its performance. For this purpose, low voltage driving, highly fine display, a high contrast ratio, a wide visual angle characteristic, a low temperature response characteristic and a wide range of driving temperature are, for example, desired. These functions have a tendency such that when some of them are improved, others have to be sacrificed.

Recently, improvement of a response speed is particularly desired. For example, in driving the device by an electrical cell, low voltage drive and high speed response are desired; in e.g. the office appliances, highly fine display and high speed response are required; and in the display for automobiles, low temperature response or high speed response within a wide temperature range for operation is desired.

In this respect, some methods for improvement are conceivable. One of them is to adopt a liquid crystal composition having a low viscosity. Namely, if the viscosity of the liquid crystal composition is reduced, the response speed can be improved so that a display will be possible at a practical speed even at a low temperature. Further, if the response speed may be at a level equal to the conventional speed, it will be possible to drive the device at a lower voltage, or a higher duty drive or highly fine drive, will be possible.

For such a purpose, a p,p'-disubstituted difluorostilbene compound has been proposed, as disclosed in Japanese Unexamined Patent Publication No. 41037/1991 or No. 294386/1991. This compound has a chemical structure as shown by the following formula (3):

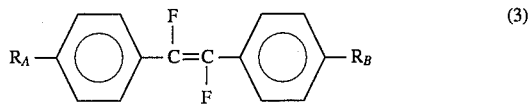

(3)

wherein each of $R_A$ and $R_B$ is a n-alkyl group, a n-alkoxy group or a n-alkoxycarbonyl group.

The compound of this formula (3) has a low viscosity and has the stability against light improved over a stilbene compound which is not substituted by fluorine. However, as compared with commonly employed liquid crystal compounds, its stability against light is still poor, and there has been drawbacks such that the useful environment is rather limited, and in many cases, it is required to use an ultraviolet ray-preventive film. Accordingly, a liquid crystal material having a low viscosity and having a high stability against light, has been desired.

It is an object of the present invention to provide a novel material thereby to solve the above problem.

The present invention provides a difluoroethylene compound of the following formula (1):

wherein $A^3$ is a trans-1,4-cyclohexylene group, and each of $A^1$, $A^2$ and $A^4$, which are independent from one another, is a trans-1,4-cyclohexylene group or a 1,4-phenylene group, wherein each of such cyclic groups is unsubstituted or substituted by one or more halogen atoms or cyano groups, one or more =CH— groups constituting rings of such cyclic groups may be substituted by nitrogen atoms, and one or more —CH₂— groups constituting rings of such cyclic groups may be substituted by oxygen atoms or sulfur atoms;

each of $Y^1$ and $Y^2$, which are independent from each other, is —COO—, —OCO—, —C≡C—, —CH₂CH₂—, —CH=CH—, —OCH₂—, —CH₂O— or a single bond;

each of m and n, which are independent from each other, is 0 or 1; and each of $R^1$ and $R^2$, which are independent from each other, is a $C_{1-10}$ alkyl group, a halogen atom or a cyano group, provided that in the case of the alkyl group, an oxygen atom, a carbonyloxy group or an oxycarbonyl group may be interposed in a carbon-carbon bond of the alkyl group or in a carbon-carbon bond between this alkyl group and the adjacent cyclic group, some of carbon-carbon bonds in the alkyl group may be triple bonds or double bonds, one —CH₂— group in the alkyl group may be substituted by a carbonyl group, and some or all of hydrogen atoms in the alkyl group may be substituted by fluorine atoms.

The present invention also provides a difluoroethylene compound of the following formula (2):

wherein $A^2$, $A^3$, $R^1$ and $R^2$ are as defined with respect to the formula (1).

Further, the present invention provides a liquid crystal compound consisting essential of a compound of the formula (1) or (2), a liquid crystal composition containing a compound of the formula (1) or (2), and a liquid crystal electro-optical device having such a liquid crystal compound or a liquid crystal composition interposed between a pair of substrates provided with electrodes.

The compound of the formula (1) of the present invention has a relatively small anisotropy of refractive index (Δn) and a low viscosity, and it is excellent in compatibility with other liquid crystals or non-liquid crystals and is a chemically stable material.

Further, the compound of the formula (1) of the present invention is a material having various properties improved over the above-mentioned compound of the formula (3). For example, it is stable against light and has improved durability, the modulus of elasticity ($K_{33}/K_{11}$) increases, so that a high contrast can be obtained, the liquid crystal upper limit temperature (Tc) increases, so that the liquid crystal temperature width can be widened, and the viscosity (η) decreases, so that a high response speed is obtainable.

Especially as a liquid crystal for high speed STN, it is superior to the compound of the formula (3) and thus is useful.

The following compounds may be mentioned to show the specific structures of the compound of the present invention. As a typical compound having two rings, the following compound may be mentioned.

$$R^1-A^2-CF=CF-A^3-R^2 \quad (4)$$

More specifically, the compound of the formula (4) includes the following compounds. In the following description, "—Ph—" represents a 1,4-phenylene group, and "—Cy—" represents a trans-1,4-cyclohexylene group. This applies not only to the compound of the formula (4) but also to other compounds.

$$R^1-Ph-CF=CF-Cy-R^2 \quad (4A)$$

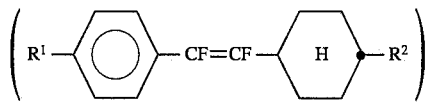

The following compound may be mentioned as a compound of the formula (4A) wherein the 1,4-phenylene group is replaced by a trans-1,4-cyclohexylene group;

$$R^1-Cy-CF=CF-Cy-R^2 \quad (4B)$$

Further, the following compound may be mentioned as a compound of the formula (4A) wherein the 1,4-phenylene group is replaced by a phenylene group with some of hydrogen atoms substituted by fluorine atoms. Here, "PhF" represents a monofluoro-1,4-phenylene group or a polyfluoro-1,4-phenylene group, and i is an integer of from 1 to 4.

$$R^1-PhF-CF=CF-Cy-R^2 \quad (4C)$$

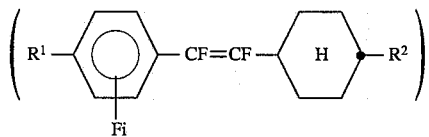

Further, as a compound having three rings, the following compound may be mentioned:

$$R^1-A^1-A^2-CF=CF-A^3-R^2 \quad (5)$$

More specifically, the compound of the formula (5) includes the following compounds.

$$R^1-Ph-Ph-CF=CF-Cy-R^2 \quad (5A)$$

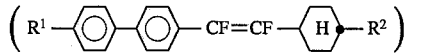

The following compounds may be mentioned as compounds of the formula (5) wherein one or two 1,4-phenylene groups are replaced by trans-1,4-cyclohexylene groups:

$$R^1-Cy-Ph-CF=CF-Cy-R^2 \quad (5B)$$
$$R^1-Ph-Cy-CF=CF-Cy-R^2 \quad (5C)$$
$$R^1-Cy-Cy-CF=CF-Cy-R^2 \quad (5D)$$

Further, the following compound may be mentioned as a compound of the formula (5) wherein the 1,4-phenylene group is a phenylene group having some hydrogen atoms substituted by fluorine atoms.

$$R^1-Ph-PhF-CF=CF-Cy-R^2 \quad (5E)$$

Further, as a compound having four rings, the following compound may be mentioned:

$$R^1-A^1-A^2-CF=CF-A^3-A^4-R^2 \quad (6)$$

More specifically, the compound of the formula (6) includes the following compounds:

$$R^1-Ph-Ph-CF=CF-Cy-Ph-R^2 \quad (6A)$$

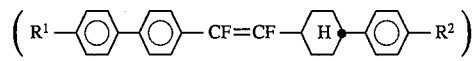

$$R^1-Cy-Ph-CF=CF-Cy-Ph-R^2 \quad (6B)$$
$$R^1-Ph-Cy-CF=CF-Cy-Ph-R^2 \quad (6C)$$
$$R^1-Cy-Cy-CF=CF-Cy-Ph-R^2 \quad (6D)$$
$$R^1-Ph-Ph-CF=CF-Cy-Cy-R^2 \quad (6E)$$
$$R^1-Cy-Ph-CF=CF-Cy-Cy-R^2 \quad (6F)$$
$$R^1-Ph-Cy-CF=CF-Cy-Cy-R^2 \quad (6G)$$
$$R^1-Cy-Cy-CF=CF-Cy-Cy-R^2 \quad (6H)$$
$$R^1-Ph-PhF-CF=CF-Cy-Ph-R^2 \quad (6I)$$

Furthermore, the following compounds may be mentioned as compounds having three or more rings wherein $Y^1$ and $Y^2$ between rings are changed to other than a single bond:

$$R^1-Ph-COO-Ph-CF=CF-Cy-R^2 \quad (5F)$$
$$R^1-Ph-OCO-Ph-CF=CF-Cy-R^2 \quad (5G)$$
$$R^1-Ph-C\equiv C-Ph-CF=CF-Cy-R^2 \quad (5H)$$
$$R^1-Ph-CH_2CH_2-Ph-CF=CF-Cy-R^2 \quad (5I)$$
$$R^1-Ph-OCH_2-Ph-CF=CF-Cy-R^2 \quad (5J)$$
$$R^1-Ph-CH_2O-Ph-CF=CF-Cy-R^2 \quad (5K)$$
$$R^1-Ph-COO-Ph-CF=CF-Cy-Ph-R^2 \quad (6J)$$
$$R^1-Ph-OCO-Ph-CF=CF-Cy-Ph-R^2 \quad (6K)$$
$$R^1-Ph-C\equiv C-Ph-CF=CF-Cy-Ph-R^2 \quad (6L)$$
$$R^1-Ph-CH_2CH_2-Ph-CF=CF-Cy-Ph-R^2 \quad (6M)$$
$$R^1-Ph-OCH_2-Ph-CF=CF-Cy-Ph-R^2 \quad (6N)$$
$$R^1-Ph-CH_2O-Ph-CF=CF-Cy-Ph-R^2 \quad (6O)$$
$$R^1-Ph-COO-Ph-CF=CF-Cy-OCO-Ph-R^2 \quad (6P)$$

Further, $A^3$ may be a group having some of hydrogen atoms of a trans-1,4-cyclohexylene group substituted by halogen atoms or cyano groups. Further, the following compounds may be mentioned as examples in which some of hydrogen atoms of the cyclic groups of $A^1$, $A^2$ and $A^4$ are substituted by halogen atoms or cyano groups, or some of =CH— groups constituting a ring are substituted by nitrogen atoms, or some of —CH$_2$— groups constituting a ring are substituted by oxygen atoms or sulfur atoms.

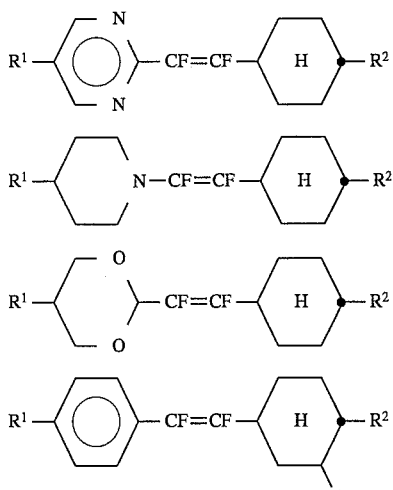

(4D)

(4E)

(4F)

(4G)

(4H)

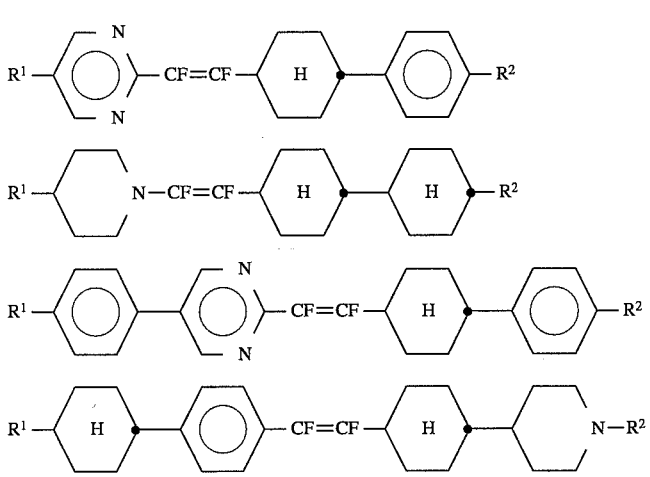

(5L)

(5M)

(6Q)

(6R)

The compound of the formula (1) of the present invention is used in the form of a liquid crystal composition prepared by mixing at least one such compound with other liquid crystal material and/or a non-liquid crystal material, whereby the liquid crystal composition can be made to have a low viscosity, and it is possible to attain a high speed response when the composition is formed into a liquid crystal display device.

The material which may be mixed with the compound of the present invention, includes, for example, the following compounds. In the following formulas, each of $R^C$ and $R^D$ represents an alkyl group, an alkoxy group, a halogen atom or a cyano group, provided that "—NON—" represents an azoxy group.

$R^C-Cy-Cy-R^D$
$R^C-Cy-Ph-R^D$
$R^C-Ph-Ph-R^D$
$R^C-Cy-COO-Ph-R^D$
$R^C-Ph-COO-Ph-R^D$
$R^C-Cy-CH=CH-Ph-R^D$
$R^C-Ph-CH=CH-Ph-R^D$
$R^C-Cy-CH_2CH_2-Ph-R^D$
$R^C-Ph-CH_2CH_2-Ph-R^D$

-continued $R^C-Ph-N=N-Ph-R^D$
$R^C-Ph-NON-Ph-R^D$
$R^C-Cy-COS-Ph-R^D$
$R^C-Cy-Ph-Ph-R^D$
$R^C-Cy-Ph-Ph-Cy-R^D$
$R^C-Ph-Ph-Ph-R^D$
$R^C-Cy-COO-Ph-Ph-R^D$
$R^C-Cy-Ph-COO-Ph-R^D$
$R^C-Cy-COO-Ph-COO-Ph-R^D$
$R^C-Ph-COO-Ph-COO-Ph-R^D$
$R^C-Ph-COO-Ph-OCO-Ph-R^D$

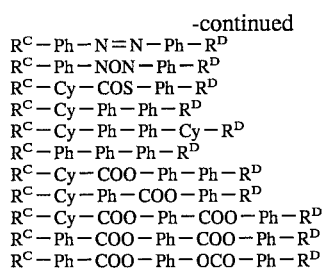

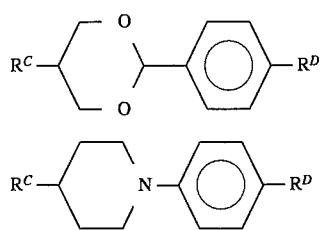

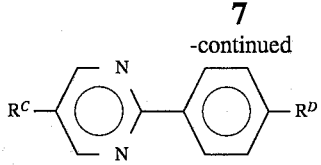

These compounds are given merely as examples. The ring structures or hydrogen atoms of the terminal groups may be substituted by halogen atoms, cyano groups or methyl groups, and the cyclohexane rings or the benzene rings may be replaced by other six-membered or five-membered rings such as pyridine rings or dioxane rings. Further, the linking group between the adjacent rings may be changed. Thus, various materials may be appropriately selected for use depending upon the desired properties.

The liquid crystal composition containing the compound of the present invention may be injected into a liquid crystal cell, so that it is interposed between a pair of substrates provided with electrodes, to constitute a liquid crystal electro-optical device.

A typical liquid crystal cell may be a twisted nematic (TN) type liquid crystal electro-optical device. Here, the term "liquid crystal electro-optical device" is used to express that it is useful not only for application to a display device but also to e.g. a light adjustable window, a light shutter or a polarizing exchanger device.

The liquid crystal electro-optical device can be used in various modes such as a twisted nematic system, a guest-host system, a dynamic scattering system, a phase change system, a DAP system, a double frequency drive system and a ferroelectric liquid crystal display system.

Now, a structure of a liquid crystal electro-optical device and a specific example for the preparation will be described.

On a substrate made of a plastic, glass or the like, an undercoat layer of $SiO_2$, $Al_2O_3$ or the like, or a color filter layer is formed as the case requires, and then an electrode of $In_2O_3$—$SnO_2$ (ITO), $SnO_2$ or the like is formed thereon, followed by patterning. Then, an overcoat layer of polyimide, polyamide, $SiO_2$ or $Al_2O_3$ is formed as the case requires, followed by orientation treatment. Then, a sealing material is printed, and the periphery is sealed so that the electrode surfaces face to each other, followed by curing the sealing material to form an empty cell.

To this empty cell, the composition containing the compound of the present invention is injected, and the injection inlet is then sealed with a sealing agent to form a liquid crystal cell. To this liquid crystal cell, a polarizing plate, a color polarizing plate, a light source, a color filter, a semi-transparent reflecting plate, a reflecting plate, a photoconducting plate, an ultraviolet ray-preventive filter or the like is laminated as the case requires, followed by printing letters or designs and by non-glare treatment, to obtain a liquid crystal electro-optical device.

The above description is intended to show merely the basic structure and the basic method for preparation of a liquid crystal electro-optical device. Various other structures may be employed, including, for example, a double layer liquid crystal cell having two liquid crystal layers with a substrate employing double layer electrodes, and an active matrix device using an active matrix substrate having a functional element such as TFT or MIM formed thereon.

By using the compound of the present invention for a liquid crystal composition, high speed response can be expected also by conducting high duty drive. Therefore, the present invention is effectively applicable to a supertwisted (STN) type liquid crystal electro-optical device having a highly twisted angle, to which an attention has been drawn in recent years. Further, the present invention is useful also for a guest-host (GH) type liquid crystal display device using multicolor colorants or a ferroelectric liquid crystal electro-optical device.

The compound of the formula (1) of the present invention can be produced, for example, by the following method.

  (7)

  (8)

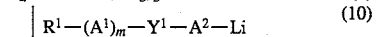  (9)

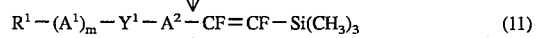  (10)

  (11)

$$\downarrow KF, H_2O$$

$R^1—(A^1)_m—Y^1—A^2—CF=CFH$  (12)

$$\downarrow n\text{-}C_4H_9Li$$

  (13)

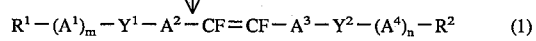  (1)

In the above formulas, $A^3$ is a trans-1,4-cyclohexylene group, and each of $A^1$, $A^2$ and $A^4$, which are independent from one another, is a trans-1,4-cyclohexylene group or a 1,4-phenylene group. Each of these cyclic groups is unsubstituted or substituted by or more halogen atoms or cyano groups. One or more =CH— groups constituting rings of such cyclic groups may be substituted by nitrogen atoms, and one or more —$CH_2$— groups constituting such rings may be substituted by oxygen atoms or sulfur atoms.

Each of $Y^1$ and $Y^2$, which are independent from each other, is —COO—, —OCO—, —C≡C—, —$CH_2CH_2$—, —CH=CH—, —$OCH_2$—, —$CH_2O$— or a single bond.

Each of m and n, which are independent from each other, is 0 or 1.

Each of $R^1$ and $R^2$, which are independent from each other, is a $C_{1-10}$ alkyl group, a halogen atom or a cyano group. In the case of an alkyl group, an oxygen atom, a carbonyloxy group or an oxycarbonyl group may be interposed in the carbon-carbon bond in this alkyl group or in the carbon-carbon bond between this alkyl group and the cyclic group. Further, some of carbon-carbon bonds in the alkyl group may be triple bonds or double bonds. Furthermore, one —$CH_2$— group in the alkyl group may be substituted by a carbonyl group, and some or all of hydrogen atoms in the alkyl group may be substituted by fluorine atoms.

X is a bromine atom or an iodine atom.

Chlorotrifluoroethylene of the formula (7) is treated with n-butyl lithium and then reacted with chlorotrimethylsilane of the formula (8) to obtain 1,1,2-trifluoro-2-trimethylsilylethylene of the formula (9). Then, without isolation, this compound (9) is reacted further with a lithium compound of the formula (10) to obtain a difluoroethylene compound of the formula (11).

The obtained compound (11) is hydrolyzed with water and potassium fluoride to obtain a difluoroethylene compound of the formula (12). This compound is treated with n-butyl lithium and then reacted with a halogen atom compound of the formula (13) to obtain a difluoroethylene compound of the formula (1).

To introduce an acyl group to $R^1$ and $R^2$ of the compound of the formula (1), a compound of the formula (1) wherein $R^1$ and $R^2$ are hydrogen atoms and an acyl halide may be subjected to a Friedel-Crafts reaction. To introduce a cyano group, a compound of the formula (1) wherein $R^1$ and $R^2$ are bromine atoms or iodine atoms may be reacted with CuCN. Further, to introduce an ethynylene group (—C≡C—) to $Y^1$ and $Y^2$ of the compound of the formula (1), a compound of the formula (1) wherein $R^1$ and $R^2$ are bromine atoms or iodine atoms and an alkynyl lithium compound may be subjected to a coupling reaction.

Now, the present invention will be described with reference to Examples. However, it should be understood that the present invention is by no means restricted by such specific Examples.

EXAMPLE 1

First step

Into a 500 ml three-necked flask equipped with a condenser and a gas supply tube, 100 ml of tetrahydrofuran (THF) was charged and cooled to –100° C. Then, 11.7 g (0.1 mol) of chlorotrifluoroethylene was introduced thereto. 62.1 ml (0.1 mol) of a n-hexane solution of n-butyl lithium (1.61M) was dropwise added thereto over a period of 30 minutes. The mixture was stirred for further 30 minutes, and then 10.9 g (0.1 mol) of chlorotrimethylsilane was dropwise added thereto.

After the dropwise addition, the mixture was stirred for one hour. Then, a THF solution of 1-lithio-4-n-propylcyclohexane separately synthesized by 20.5 g (0.1 mol) of 1-bromo-4-n-propylcyclohexane and 0.76 g (0.11 mol) of metal lithium, was dropwise added thereto at –100° C. The mixture was further stirred for two hours at 0° C. Then, a dilute hydrochloric acid aqueous solution was added thereto. The organic layer was separated. The aqueous layer was extracted with methylene chloride, and the organic layers were put together and dried. Then, the solvent was distilled off to obtain 18.2 g (yield: 70%) of (Z)-1,2-difluoro-1-(trans-4-n-propylcyclohexyl)-2-trimethylsilyl ethylene.

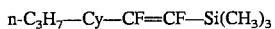

n-C$_3$H$_7$—Cy—CF=CF—Si(CH$_3$)$_3$

Second step

Then, 18.2 g (0.07 mol) of the obtained (Z)-1,2-difluoro-1-(trans-4-n-propylcyclohexyl)-2-trimethylsilylethylene was dissolved in 50 ml of acetonitrile, and then 8.12 g (0.14 mol) of potassium fluoride and 3.78 g (0.21 mol) of water were added thereto. The mixture was reacted for one hour at 50° C. The reaction mixture was cooled, and then 200 ml of water was added thereto. The mixture was extracted with methylene chloride. The organic layer was washed with a saturated sodium chloride aqueous solution and dried over CaCl$_2$. After filtration, the solvent and low boiling substances were distilled off, and the residue was further distilled under reduced pressure to obtain 10.5 g (yield: 80%) of (E)-1,2-difluoro-1-(trans-4-n-propylcyclohexyl)ethylene.

n-C$_3$H$_7$—Cy—CF=CFH

Third step

Then, 10.5 g (0.056 mol) of the obtained (E)-1,2-difluoro-1-(trans-4-n-propylcyclohexyl)ethylene was dissolved in 50 ml of THF, and the solution was cooled to –30° C. Then, 34.8 ml (0.056 mol) of a n-hexane solution of n-butyl lithium (1.61M) was dropwise added thereto over a period of 30 minutes. The mixture was stirred for further 30 minutes, and then 12.6 g (0.062 mol) of 1-bromo-4-n-propylcyclohexane was dropwise added at –30° C.

The mixture was stirred for further one hour, and then a dilute hydrochloric acid aqueous solution was added to the reaction solution. The organic layer was separated. The aqueous layer was extracted with methylene chloride, and the organic layers were put together and dried. Then, the solvent was distilled off, and the obtained crude crystals were purified by silica gel column chromatography to obtain 13.1 g (yield: 75%) of trans-1,2-difluoro-1,2-bis(trans-4-n-propylcyclohexyl)ethylene.

| $^{19}$F NMR(CDCl$_3$) | –155.8 ppm (d, J$_{H-F}$ = 27 Hz) δ ppm from CFCl$_3$ |
|---|---|
| MS | m/e 312 (M$^+$) |
| IR | 1230 cm$^{-1}$ (C—F) |

The analytical results of this compound will be shown below. Here, d means "doublet".

| $^{19}$F NMR(CDCl$_3$) | –155.8 ppm (d, J$_{H-F}$ = 27 Hz) δ ppm from CFCl$_3$ |
|---|---|
| MS | m/e 312 (M$^+$) |
| IR | 1230 cm$^{-1}$ (C—F) |

In the same manner as in Example 1, the following compounds can be prepared.

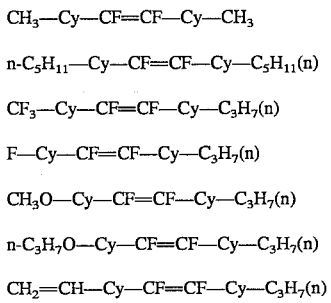

CH$_3$—Cy—CF=CF—Cy—CH$_3$ n-C$_5$H$_{11}$—Cy—CF=CF—Cy—C$_5$H$_{11}$(n)

CF$_3$—Cy—CF=CF—Cy—C$_3$H$_7$(n)

F—Cy—CF=CF—Cy—C$_3$H$_7$(n)

CH$_3$O—Cy—CF=CF—Cy—C$_3$H$_7$(n)

n-C$_3$H$_7$O—Cy—CF=CF—Cy—C$_3$H$_7$(n)

CH$_2$=CH—Cy—CF=CF—Cy—C$_3$H$_7$(n)

EXAMPLE 2

The reactions were conducted in the same manner as in Example 1 except that in the first step in Example 1, 24.6 g (0.1 mol) of 1-iodo-4-n-propylbenzene was used instead of 1-bromo-4-n-propylcyclohexane, to obtain 9.2 g (yield: 31%) of trans-1,2-difluoro-1-(4-n-propylphenyl)-2-(trans-4-n-propylcyclohexyl)ethylene.

n-C$_3$H$_7$—Ph—CF=CF—Cy—C$_3$H$_7$(n)

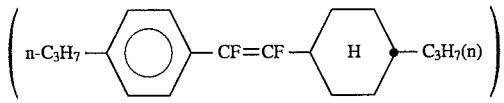

The analytical results of this compound will be shown below.

$^{19}$F NMR (CDCl$_3$) –159.8 ppm (d, J$_{H-F}$=132 Hz), –139.6 ppm (d, d, J$_{H-F}$=132 Hz, J$_{H-F}$=27 Hz) δ ppm from CFCl$_3$ MS m/e 306(M$^+$)

IR 1230 cm$^{-1}$ (C—F)

In the same manner as in Example 2, the following compounds can be prepared.

CH$_3$—Ph—CF=CF—Cy—CH$_3$ n-C$_5$H$_{11}$—Ph—CF=CF—Cy—C$_5$H$_{11}$(n)

CF$_3$—Ph—CF=CF—Cy—C$_3$H$_7$(n)

F—Ph—CF=CF—Cy—C$_3$H$_7$(n)

CH₃O—Ph—CF=CF—Cy—C₃H₇(n)

n-C₃H₇O—Ph—CF=CF—Cy—C₃H₇(n)

CH₂=CH—Ph—CF=CF—Cy—C₃H₇(n)

EXAMPLE 3

The reactions were conducted in the same manner as in Example 1 except that in the first step of Example 1, 23.6 g (0.1 mol) of 1,4-dibromobenzene was used instead of 1-bromo-4-n-propylcyclohexane, to obtain 11.0 g (yield: 32%) of trans-1,2-difluoro-1-(4-bromophenyl)-2-(trans-4-n-propylcyclohexyl)ethylene.

Br—Ph—CF=CF—Cy—C₃H₇(n)

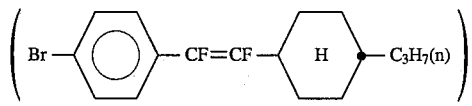

The analytical results of this compound will be shown below.

MS m/e 343(M⁺)

IR 1230 cm⁻¹ (C—F)

In the same manner as in Example 3, the following compound can be prepared.

Br—Cy—CF=CF—Cy—C₃H₇(n)

Comparative Example 1

Into a 200 ml three-necked flask equipped with a condenser and a gas supply tube, 2.46 g (10 mmol) of 1-iodo-4-n-propylbenzene, 2.36 g (10 mmol) of 1,4-dibromobenzene and 50 ml of diethyl ether were introduced and cooled to −78° C. Then, 12.4 ml (20 mmol) of a n-hexane solution of n-butyl lithium (1.61M) was dropwise added thereto over a period of 30 minutes. The mixture was stirred for further 30 minutes. Then, 10 g (0.1 mol) of tetrafluoroethylene was blown thereinto while raising the temperature to 10° C.

The mixture was further stirred at room temperature for one hour. Then, a dilute hydrochloric acid aqueous solution was added thereto. The organic layer was separated. The aqueous layer was extracted with diethyl ether, and the organic layers were put together and dried. Then, the solvent was distilled off to obtain 0.27 g (yield: 8%) of 1,2-difluoro-1-(4-bromophenyl)-2-(4-n-propylphenyl)ethylene.

As is evident from Example 3 and Comparative Example 1, the compound of the present invention is more advantageous than a difluorostilbene type compound also in the yield.

EXAMPLE 4

Into a 300 ml three-necked flask equipped with a condenser, 0.90 g (0.01 mol) of CuCN and 50 ml of dry dimethylsulfoxide (DMSO) were introduced, heated to 90° C. and dissolved. Then, a DMSO solution containing 3.43 g (0.01 mol) of trans-1,2-difluoro-1-(4-bromophenyl)-2-(trans-4-n-propylcyclohexyl)ethylene obtained in Example 3, was dropwise added thereto under stirring. Then, the mixture was stirred for further one hour at 150° C. and then cooled to room temperature.

200 ml of water was poured thereto. The mixture was extracted with methylene chloride, and the organic layer was washed with a saturated sodium chloride aqueous solution and dried over CaCl₂. After filtration, the solvent was distilled off, and the obtained solid was purified by silica gel column chromatography to obtain 2.57 g (yield: 89%) of trans-1,2-difluoro-1-(4-cyanophenyl)-2-(trans-4-n-propylcyclohexyl)ethylene.

NC—Ph—CF=CF—Cy—C₃H₇(n)

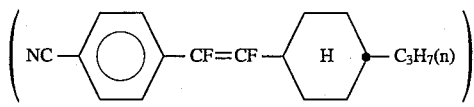

The analytical results of this compound will be shown below.

MS m/e 289 (M⁺)

IR 1230 cm⁻¹ (C—F), 2230 cm⁻¹ (C≡N)

EXAMPLE 5

The reactions were conducted in the same manner as in Example 1 except that in the first step of Example 1, 17.5 g (0.1 mol) of 5-methylpyrimidyl bromide was used instead of 1-bromo-4-n-propylcyclohexane, to obtain 8.5 g (yield: 30%) of trans-1,2-difluoro-1-(5-methylpyrimidin-2-yl)-2-(trans-4-n-propylcyclohexyl)ethylene. Here, "—Py—" represents a pyrimidin-2,5-diyl group.

CH₃—Py—CF=CF—Cy—C₃H₇(n)

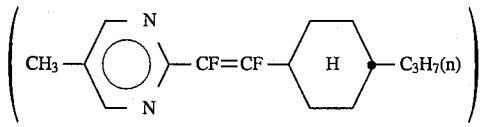

The analytical results of this compound will be shown below.

MS m/e 282 (M⁺)

IR 1230 cm⁻¹ (C—F)

In the same manner as in Example 5, the following compounds can be prepared.

n-C₃H₇—Py—CF=CF—Cy—C₃H₇(n)

CH₃O—Py—CF=CF—Cy—C₃H₇(n)

n-C₃H₇O—Py—CF=CF—Cy—C₃H₇(n)

EXAMPLE 6

The reactions were conducted in the same manner as in Example 1 except that in the first step of Example 1, 28.1 g (0.1 mol) of trans-1-bromo-4-(4-n-propylphenyl)cyclohexane was used instead of 1-bromo-4-n-propylcyclohexane, to obtain 14.7 g (yield: 38%) of trans-1,2-difluoro-1-(trans-4-propylcyclohexyl)-2-[4-(trans-4-n-propylphenyl)cyclohexyl]ethylene.

n-C₃H₇—Ph—Cy—CF=CF—Cy—C₃H₇(n)

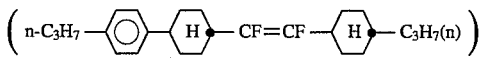

The analytical results of this compound will be shown below.
MS m/e 388 (M$^+$)
IR 1230 cm$^{-1}$ (C—F)

In the same manner as in Example 6, the following compounds can be prepared.

n-C$_3$H$_7$—Ph—Ph—CF=CF—Cy—C$_3$H$_7$(n)

n-C$_3$H$_7$—Cy—Ph—CF=CF—Cy—C$_3$H$_7$(n)
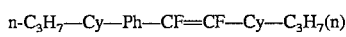

n-C$_3$H$_7$—Cy—Cy—CF=CF—Cy—C$_3$H$_7$(n)
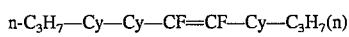

EXAMPLE 7

The reactions were conducted in the same manner as in Example 1 except that in the first step of Example 1, 24.6 g (0.1 mol) of 1-iodo-4-n-propylbenzene was used instead of 1-bromo-4-n-propylcyclohexane, and in the third step, 10.9 g (0.038 mol) of trans-1-bromo-4-(4-n-propylcyclohexyl)cyclohexane was used instead of 1-bromo-4-n-propylcyclohexane, to obtain 10.5 g (yield: 27%) of trans-1,2-difluoro-1-(4-propylphenyl)-2-[4-(trans-4-n-propylcyclohexyl)cyclohexyl]ethylene.

n-C$_3$H$_7$—Ph—CF=CF—Cy—Cy—C$_3$H$_7$(n)
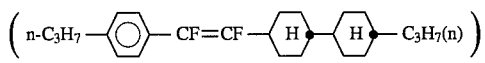

The analytical results of this compound will be shown below.
MS m/e 388 (M$^+$)
IR 1230 cm$^{-1}$ (C—F)

In the same manner as in Example 7, the following compound can be prepared.

n-C$_3$H$_7$—Ph—CF=CF—Cy—Ph—C$_3$H$_7$(n)

EXAMPLE 8

Into a 100 ml three-necked flask equipped with a reflux condenser, 0.13 g (0.0055 mol) of magnesium and 10 ml of dry THF were introduced under an argon atmosphere. Then, a few drops of 1-bromopropane was added thereto, and 1.01 g (0.0055 mol) of 4-methylphenethyl bromide was further dropwise added at a rate where heat generation continued. After completion of the dropwise addition, the mixture was refluxed for further one hour and then left to cool to room temperature.

Separately, into a 100 ml three-necked flask equipped with a refluxed condenser, 1.72 g (0.005 mol) of trans-1,2-difluoro-1-(4-bromophenyl)-2-(trans-4-n-propylcyclohexyl)ethylene obtained in Example 3 and 20 ml of a dry THF solution containing 0.1 g of 1,3-bis(diphenylphosphino)propanedichloronickel [NiCl$_2$ (DPPP)] were introduced under an argon atmosphere, and the above solution was dropwise added thereto by means of a dropping funnel.

After the dropwise addition, the mixture was stirred at room temperature for 24 hours. Then, 20 ml of water was added thereto. Further, 20 ml of 20% hydrochloric acid was added. Then, the organic layer was separated, washed with water and dried, and then the solvent was distilled off. The obtained crude product was purified by silica gel column chromatography to obtain 1.15 g (yield: 60%) of trans-1,2-difluoro-1-[4-(4-methylphenethyl)phenyl]-2-(trans-4-n-propylcyclohexyl)ethylene.

CH$_3$—Ph—CH$_2$CH$_2$—Ph—CF=CF—Cy—C$_3$H$_7$(n)
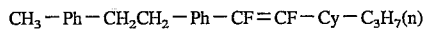
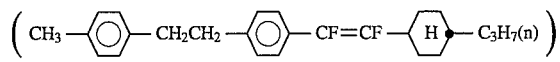

The analytical results of this compound will be shown below.
MS m/e 382 (M$^+$)
IR 1230 cm$^{-1}$ (C—F)

In the same manner as in Example 8, the following compounds can be prepared.

CH$_3$—Ph—CH$_2$CH$_2$—Cy—CF=CF—Cy—C$_3$H$_7$(n)
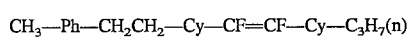

CH$_3$O—Ph—CH$_2$CH$_2$—Ph—CF=CF—Cy—C$_3$H$_7$(n)
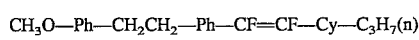

EXAMPLE 9

The reactions were conducted in the same manner as in Example 8 except that in Example 8, 1.08 g (0.0055 mol) of 1-bromo-2-(4-methylphenyl)ethene was used instead of 4-methylphenethyl bromide, to obtain 1.24 g (yield: 65%) of trans-1,2-difluoro-1-[4-(2-p-methylphenylethenyl)phenyl]-2-(trans-4-n-propylcyclohexyl)ethylene.

CH$_3$—Ph—CH=CH—Ph—CF=CF—Cy—C$_3$H$_7$(n)
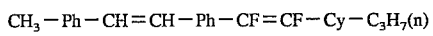
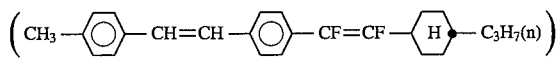

The analytical results of this compound will be shown below.
MS m/e 380 (M$^+$)
IR 1230 cm$^{-1}$ (C—F)

In the same manner as in Example 9, the following compounds can be prepared.

CH$_3$—Ph—CH=CH—Cy—CF=CF—Cy—C$_3$H$_7$(n)
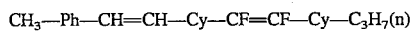

CH$_3$O—Ph—CH=CH—Ph—CF=CF—Cy—C$_3$H$_7$(n)
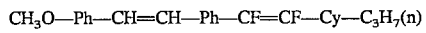

EXAMPLE 10

The reactions were conducted in the same manner as in Example 1 except that in the first step of Example 1, 27.1 g (0.1 mol) of 4-bromo-4'-methyltrane was used instead of 1-bromo-4-n-propylcyclohexane, to obtain 10.2 g (yield: 27%) of trans-1,2-difluoro-1-[4-(2-p-tolylethynyl)phenyl]-2-(trans-4-n-propylcyclohexyl)ethylene.

CH$_3$—Ph—C≡C—Ph—CF=CF—Cy—C$_3$H$_7$(n)
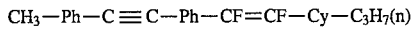
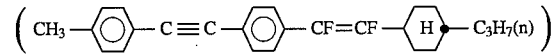

The analytical results of this compound will be shown below.
MS m/e 378 (M$^+$)
IR 1230 cm$^{-1}$ (C—F)

In the same manner as in Example 10, the following compounds can be prepared.

CH$_3$—Ph—C≡C—Cy—CF=CF—Cy—C$_3$H$_7$(n)
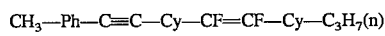

CH$_3$O—Ph—C≡C—Ph—CF=CF—Cy—C$_3$H$_7$(n)
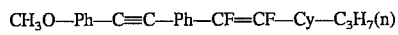

EXAMPLE 11

The reactions were conducted in the same manner as in Example 1 except that in the first step of Example 1, 4-iodophenyltetrahydropyranyl ether was used instead of 1-bromo-4-n-propylcyclohexane, and the product was finally treated with an acid to obtain 8.4 g (yield: 29%) of trans-1,2-difluoro-1-(4-hydroxyphenyl)-2-(trans-4-n-propylcyclohexyl)ethylene.

Then, 2.80 g (0.01 mol) of the obtained trans-1,2-difluoro-1-(4-hydroxyphenyl)-2-(trans-4-n-propylcyclohexyl)ethylene, 1.52 g of potassium carbonate and 30 ml of acetone were mixed, and 2.79 g of α-bromo-p-xylene was further dropwise added thereto at room temperature. The mixture was refluxed for 4 hours, then cooled and filtered. The solvent was distilled off, and the obtained crude crystals were purified by silica gel column chromatography to obtain 3.65 g (yield: 95%) of trans-1,2-difluoro-1-[4-(4-methylbenzyloxy)phenyl]-2-(trans-4-n-propylcyclohexyl)ethylene.

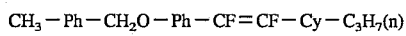

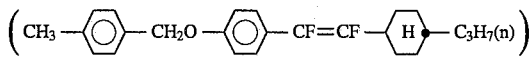

The analytical results of this compound will be shown below.

MS m/e 384 (M⁻)

IR 1230 cm⁻¹ (C—F)

In the same manner as in Example 11, the following compounds can be prepared.

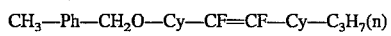

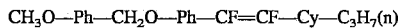

EXAMPLE 12

2.80 g (0.01 mol) of trans-1,2-difluoro-1-(4-hydroxyphenyl)-2-(trans-4-n-propylcyclohexyl)ethylene obtained in Example 11, was dissolved in 20 ml of $CH_2Cl_2$, and 0.87 g of pyridine was added thereto at room temperature. The mixture was cooled to 0° C., and 1.70 g of p-toluoyl chloride was dropwise added thereto.

The mixture was stirred at room temperature for one hour and cooled. Then, dilute hydrochloric acid was added thereto, and the mixture was filtered. Then, the solvent was distilled off, the obtained crude crystals were purified by silica gel column chromatography to obtain 3.70 g (yield: 93%) of trans-1,2-difluoro-1-[4-(4-methylbenzoyloxy)phenyl]-2-(trans-4-n-propylcyclohexyl)ethylene.

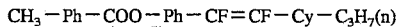

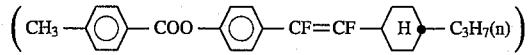

The analytical results of this compound will be shown below.

MS m/e 398 (M⁺)

IR 1230 cm⁻¹ (C—F), 1720 cm⁻¹ (C=O)

In the same manner as in Example 12, the following compounds can be prepared.

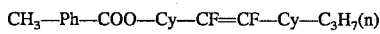

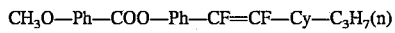

EXAMPLE 13

To 80 wt % of a liquid crystal composition "ZLI-1565" manufactured by Merck Co., 20 wt % of the compound of Example 1 of the present invention was added to obtain a liquid crystal composition. As Comparative Examples, a liquid crystal composition composed solely of the liquid crystal composition "ZLI-1565" manufactured by Merck Co. (Comparative Example 2) and a liquid crystal composition prepared by adding 20 wt % of trans-4,4'-bis-(n-propyl)difluorostilbene to 80 wt % of the liquid crystal composition "ZLI-1565" manufactured by Merck Co. (Comparative Example 3) were prepared. These liquid crystal compositions were respectively sealed in liquid crystal cells provided with poralizing plates to obtain STN type liquid crystal display devices.

The display properties of the liquid crystal display devices of Example 13 and Comparative Example 3 were almost equal, and high speed responses were obtained as compared with the device of Comparative Example 2. Then, the liquid crystal display devices of Example 13 and Comparative Example 3 were irradiated by an ultraviolet ray carbon arc lamp for 200 hours. After irradiation, the liquid crystal compositions in the respective devices were analyzed.

As a result, in the case of the liquid crystal composition of Example 13, no substantial formation of a new compound was observed. On the other hand, in the case of the liquid crystal composition of Comparative Example 3, generation of cis-4,4'-bis-(n-propyl)difluorostilbene was observed.

The compound of the formula (1)

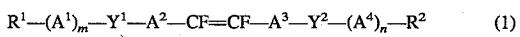

of the present invention, wherein $A^1$ to $A^4$, $R^1$, $R^2$, $Y^1$, $Y^2$, m and n are as defined above, has a relatively small anisotropy of refractive index (Δn) and a low viscosity and is excellent in the compatibility with other liquid crystals or non-liquid crystals and a chemically stable material, and when used as a liquid crystal composition, it improves the response speed even when added in a small amount, whereby low voltage drive, high duty drive and wide temperature range operation will be made possible.

Further, it is a material having various properties improved, such that it is more stable to light than a difluorostilbene type liquid crystal, so that the durability will be improved, the modulus of elasticity ($K_{33}/K_{11}$) increases, so that a high contrast will be obtained, the liquid crystal upper limit temperature (Tc) increases, so that the liquid crystal temperature width will be widened, and the viscosity (η) decreases, so that high speed response will be obtained.

Especially, as a liquid crystal material for high speed STN, it is superior to the difluorostilbene type liquid crystal and thus is useful.

What is claimed is:

1. A compound selected from difluoroethylene derivatives of the following formula (1):

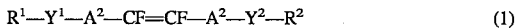

wherein $A^3$ is a trans-1,4-cyclohexylene group and $A^2$ is a 1,4-phenylene group;

each of $Y^1$ and $Y^2$ is a single bond;

each of $R^1$ and $R^2$, which are independent from each other, is an unsubstituted $C_{1-10}$ alkyl group.

* * * * *